(12) United States Patent
Miyatani

(10) Patent No.: US 10,488,303 B2
(45) Date of Patent: Nov. 26, 2019

(54) REPLACEMENT BLADE SUPPLYING MECHANISM

(71) Applicant: SAKURA FINETEK JAPAN CO., LTD., Tokyo (JP)

(72) Inventor: Tatsuya Miyatani, Tokyo (JP)

(73) Assignee: SAKURA FINETEK JAPAN CO., LTD., Tokyo (JP)

(*) Notice: Subject to any disclaimer, the term of this patent is extended or adjusted under 35 U.S.C. 154(b) by 0 days.

(21) Appl. No.: 14/437,056

(22) PCT Filed: Oct. 25, 2013

(86) PCT No.: PCT/JP2013/078951
§ 371 (c)(1),
(2) Date: Apr. 20, 2015

(87) PCT Pub. No.: WO2014/073393
PCT Pub. Date: May 15, 2014

(65) Prior Publication Data
US 2015/0268134 A1    Sep. 24, 2015

(30) Foreign Application Priority Data

Nov. 8, 2012    (JP) .................................. 2012-246337

(51) Int. Cl.
| | | |
|---|---|---|
| G01N 1/06 | (2006.01) | |
| B26D 7/26 | (2006.01) | |
| B23Q 3/155 | (2006.01) | |

(52) U.S. Cl.
CPC ............. *G01N 1/06* (2013.01); *B23Q 3/1556* (2013.01); *B26D 7/2614* (2013.01); *G01N 2001/065* (2013.01); *Y10T 483/136* (2015.01)

(58) Field of Classification Search
CPC .......... B65D 83/10; B65D 85/62; G07F 11/04
See application file for complete search history.

(56) References Cited

U.S. PATENT DOCUMENTS

| | | | | |
|---|---|---|---|---|
| 4,207,790 A | * | 6/1980 | Endo ........................ | G01N 1/06 83/699.11 |
| 5,107,731 A | * | 4/1992 | Kent ........................ | B26D 3/28 83/77 |

(Continued)

FOREIGN PATENT DOCUMENTS

| | | |
|---|---|---|
| CN | 1195597 | 10/1998 |
| CN | 1991329 | 7/2007 |

(Continued)

OTHER PUBLICATIONS

Notice of Allowance from corresponding Japanese Application No. 2012-246337 dated Sep. 6, 2016. English translation attached.

(Continued)

*Primary Examiner* — Gene O Crawford
*Assistant Examiner* — Kevin L Randall, Jr.
(74) *Attorney, Agent, or Firm* — Grossman, Tucker, Perreault & Pfleger, PLLC

(57) ABSTRACT

A replacement blade supplying mechanism (51) includes a detection portion (75) which detects whether or not there is a cutting blade (21) in a layer below an uppermost cutting blade (21d) through a through hole (21b) of the uppermost cutting blade (21d) when the uppermost cutting blade (21d) is extruded by a lever portion (54), and when the detection portion (75) detects that there is no cutting blade (21) in a layer below the uppermost cutting blade (21d), the detection portion stops the transport of the cutting blade (21) by a cutting blade transport mechanism (26).

3 Claims, 12 Drawing Sheets

(56) References Cited

U.S. PATENT DOCUMENTS

| | | | |
|---|---|---|---|
| 5,851,213 A | 12/1998 | Berleth et al. | |
| 5,857,588 A * | 1/1999 | Kasper | B65H 3/24 221/232 |
| 5,937,522 A * | 8/1999 | Althaus | B26B 21/24 206/354 |
| 6,196,897 B1 | 3/2001 | Suto et al. | |
| 2002/0005104 A1 | 1/2002 | Hendrick et al. | |
| 2003/0116583 A1* | 6/2003 | Pugh | C01N 33/48757 221/268 |
| 2008/0202308 A1* | 8/2008 | Fujiwara | G01N 1/06 83/703 |
| 2010/0032891 A1* | 2/2010 | Togashi | B65H 3/047 271/18.1 |
| 2011/0031679 A1* | 2/2011 | Fujita | B65H 1/14 271/90 |
| 2011/0040165 A1* | 2/2011 | Williams | A61B 5/157 600/365 |
| 2012/0017449 A1 | 1/2012 | Bro | |
| 2013/0104628 A1* | 5/2013 | Colston | B65H 3/0808 73/37 |
| 2014/0034665 A1* | 2/2014 | Walter | B65D 83/08 221/102 |
| 2014/0263385 A1* | 9/2014 | Martin | G06Q 20/18 221/1 |
| 2014/0361034 A1* | 12/2014 | Peyrot | B65D 83/0817 221/279 |
| 2015/0310694 A1* | 10/2015 | Will | G07F 11/165 221/13 |
| 2015/0362352 A1* | 12/2015 | Garrepy | G01N 21/78 73/37 |

FOREIGN PATENT DOCUMENTS

| | | |
|---|---|---|
| CN | 101369123 | 2/2009 |
| CN | 101837388 | 9/2010 |
| CN | 102165301 | 8/2011 |
| JP | 2010-054483 | 3/2010 |
| JP | 2010-249724 | 11/2010 |
| JP | 2010-261794 | 11/2010 |
| WO | 2014/073393 | 5/2014 |

OTHER PUBLICATIONS

International Search Report from corresponding PCT Application No. PCT/JP2013/078951 dated Nov. 26, 2013. English translation attached.

Extended European Search Report from corresponding EPO Application No. 13853776.6 dated Jun. 3, 2016.

Office Action from related Chinese Application No. 201380055448.7 dated May 31, 2016. English translation of Search Report only.

* cited by examiner

REPLACEMENT BLADE SUPPLYING MECHANISM

TECHNICAL FIELD

The present invention relates to a replacement blade supplying mechanism.

Priority is claimed on Japanese Patent Application No. 2012-246337, filed Nov. 8, 2012, the content of which is incorporated herein by reference.

BACKGROUND ART

As one of methods for inspecting and observing a biological sample extracted from a human body, experimental animal, or the like, a method is known in which a thin section is prepared from an embedding block in which the biological sample is embedded by an embedding agent, dye processing is performed on the thin section, and thus, the biological sample is observed.

In the related art, an operation of preparing the thin section is performed manually by an experienced operator using a sharp and thin cutting blade. However, in recent years, an automatic slicing device capable of automatically performing the operation of preparing the thin section has begun to be provided. According to this automatic thin-cutting device, it is possible to continuously prepare the thin sections without imposing a burden on the operator.

However, when the embedding block is thinly cut and the thin section is prepared, in order to prepare a thin section having high quality, it is necessary to thinly cut the embedding block to a predetermined thickness (for example, 3 μm to 5 μm). Accordingly, particularly, an operator pays attention to sharpness of the cutting blade. When the thin cutting is performed in a state where the sharpness of the cutting blade deteriorates, it is not easy to thinly cut the embedding block to a desired thickness. In addition, in some cases, there is a concern that the thin section may be damaged. In this way, since some disadvantages occur, it is necessary that the operator periodically replaces the cutting blade.

Here, for example, in PTLs 1 and 2, a configuration is disclosed which includes a cutting blade transport mechanism which feeds a plurality of cutting blades accommodated in a replacement blade cartridge one by one and transports the cutting blades to a holder, and prepares the thin section by thinly cutting an embedding block while automatically replacing the cutting blade.

As shown in FIG. 16, a replacement blade cartridge 100 includes a case main body 102, a lever portion 103, and an opening portion 104. The case main body 102 accommodates a plurality of cutting blades 101 in a state where the cutting blades overlap with one another. The lever portion 103 extrudes an uppermost cutting blade 101a positioned in the uppermost layer among the plurality of cutting blades 101 accommodated in the case main body 102, along an extension direction of the uppermost cutting blade 101a. The opening portion 104 is formed on a side surface positioned in front of the uppermost cutting blade 101a extruded by the lever portion 103, in the case main body 102, and the uppermost cutting blade 101a passes through the opening portion 104.

Moreover, a biasing portion 105, which biases the cutting blades 101 toward the upper layer in the overlapping direction, is provided between the bottom surface of the case main body 102 and a lowermost cutting blade 101b positioned in the lowermost layer among the plurality of cutting blades 101. For example, the biasing portion 105 is a V-shaped plate spring, and the center portion of the biasing portion 105 is fixed to the bottom surface of the case main body 102. Both end portions of the biasing portion 105 support both end portions of the lowermost cutting blade 101b in the direction, in which the blade edge of the lowermost cutting blade 101b extends, from below.

In this case, the lever portion 103 is moved by a cutting blade transport mechanism (not shown), only the uppermost cutting blade 101a accommodated in the case main body 102 is extruded, and thus, the uppermost cutting blade 101a is transported outside the case main body 102 from the opening portion 104 of the case main body 102.

CITATION LIST

Patent Literature

[PTL 1] Japanese Unexamined Patent Application, First Publication No. 2010-261794

SUMMARY OF INVENTION

Technical Problem

However, in the above-described replacement blade cartridge 100 in the related art, failure in supply of the lowermost cutting blade 101b from the cutting blades 101 accommodated in the case main body 102 may occur. That is, as shown in FIG. 17, in a state where only one of the cutting blades 101 accommodated in the case main body 102 remains (in a state where only the lowermost cutting blade 101b remains), when the lowermost cutting blade 101b is extruded by the lever portion 103, contact between one end portion (the rear end portion in the transport direction) of the lowermost cutting blade 101b and the biasing portion 105 is released during the transport.

Accordingly, as shown in FIG. 18, since only the other end portion (the front end portion in the transport direction) of the lowermost cutting blade 101b is supported by the biasing portion 105, the lowermost cutting blade 101b is inclined in the transport direction. According to this, pressing between the lowermost cutting blade 101b and the lever portion 103 is released, and as a result, the lowermost cutting blade 101b cannot be transported, and even when the pressing between the lowermost cutting blade and the lever portion 103 is maintained, the lowermost cutting blade 101b is transported in a direction different from a desired transport direction. When the failure in the supply of the lowermost cutting blade 101b is caused in this state, it is difficult to determine an operation during which the lowermost cutting blade 101b stops, and thus, it is not possible to determine an abnormal location or a cause of abnormality in the device. Accordingly, it is necessary to stop the entire automatic thin-cutting device, and a replacement operation of the replacement blade cartridge 100 takes a lot of time.

Meanwhile, it is considered that a plate which is a dummy may be provided between the biasing portion 105 and the lowermost cutting blade 101b.

In this case, the lowermost cutting blade 101b is supported by the biasing portion 105 via the plate. Accordingly, it is considered that the cutting blades 101 can be used to the last one.

However, in this case, since a dedicated replacement blade cartridge is required, there is a problem that a degree of freedom with respect to selection of the cutting blade 101 by an operator is limited.

Therefore, an aspect of the present invention is made in consideration of the above-described circumstances, and an object thereof is to provide a replacement blade supplying mechanism capable of preventing failure in supply of the cutting blade before it happens, and of improving a degree of freedom with respect to selection of a cutting blade.

Solution to Problem

A replacement blade supplying mechanism of the present invention adopts the following means.

(1) According to an aspect of the present invention, there is provided a replacement blade supply mechanism including a transport mechanism in which a replacement blade cartridge in which a plurality of cutting blades having a blade edge on one end are accommodated in a thickness direction along is detachably set, and an uppermost cutting blade positioned in the uppermost layer among the cutting blades accommodated in the replacement blade cartridge is transported individually in a direction in which the blade edge extends, in which the transport mechanism includes a detection portion which detects whether or not there is a cutting blade in a layer below an uppermost cutting blade through a portion through which the uppermost cutting blade passes when the uppermost cutting blade is transported, and when the detection portion detects that there is no cutting blade in a layer below the uppermost cutting blade, the detection portion stops the transport of the cutting blade.

According to this configuration, when the detection portion detects that there is no cutting blade in a layer below the uppermost cutting blade, the detection portion stops the transport of the cutting blade. Accordingly, it is possible to prompt an operator to replace the replacement blade cartridge in a state where the last one of the cutting blades accommodated in the replacement blade cartridge remains.

Therefore, even when a cutting blade accommodated in the replacement blade cartridge is biased upward via the lowermost cutting blade positioned in the lowermost layer by the biasing portion, it is possible to stop the transport of the cutting blade (lowermost cutting blade) before the biasing with respect to the lowermost cutting blade by the biasing portion is released. Accordingly, it is possible to prevent failure in supply of the cutting blade such as a case where the cutting blade cannot be transported or a case where the cutting blade is transported in a direction different from a desired transport direction before it happens. In addition, even when the transport of the cutting blade stops, it is possible to easily check an abnormal location or a cause of abnormality in the device, and it is possible to smoothly perform a replacement operation of the replacement blade cartridge.

Moreover, since it is not necessary to dispose a plate which is a dummy between the biasing portion and the lowermost cutting blade in order to prevent failure in the supply of the cutting blade, it is possible to improve a degree of freedom with respect to selection of the cutting blade.

(2) In the replacement blade supplying mechanism of (1), the transport mechanism may include a cartridge accommodation portion which accommodates a case main body in which the cutting blades are accommodated, in the replacement blade cartridge; and a lever guide which accommodates a lever portion which extrudes the uppermost cutting blade in the direction in which the blade edge extends, and relatively moves the lever portion in the direction, in which the blade edge of the cutting blade extends, with respect to the case main body, in the replacement blade cartridge, in which a regulation portion which extends along a movement direction of the lever guide may be formed on an opening edge of the lever guide.

According to this configuration, since the regulation portion which extends along the movement direction of the lever guide is formed, in the movement direction of the lever guide, it is possible to prevent the replacement blade cartridge from being set in a state where the lever portion is positioned at locations other than the lever guide. In addition, the operator can easily determine the set location of the lever portion. Accordingly, it is possible to prevent the replacement blade cartridge from being erroneously set, and it is possible to more smoothly perform the replacement operation of the replacement blade cartridge.

Advantageous Effects of Invention

According to a replacement blade supplying mechanism of the aspects of the present invention, it is possible to prevent failure in supply of a cutting blade before it happens, and it is possible to improve a degree of freedom with respect to selection of the cutting blade.

DESCRIPTION OF EMBODIMENTS

Next, an embodiment of the present invention will be described with reference to the drawings.

<Configuration of Automatic Thin-Cutting Device>

Figure 1:
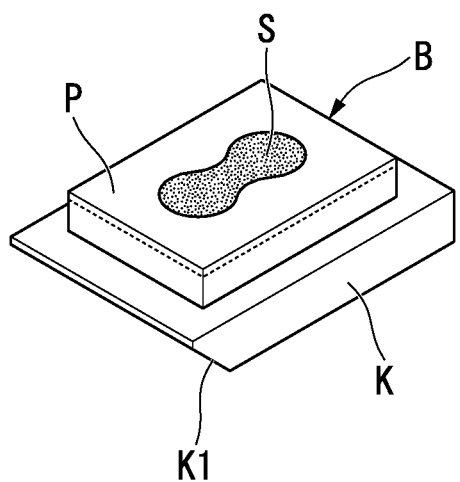
FIG. 1 is a perspective view of an embedding block and a cassette which are transported by an automatic thin-cutting device according to the present invention.
Figure 2:
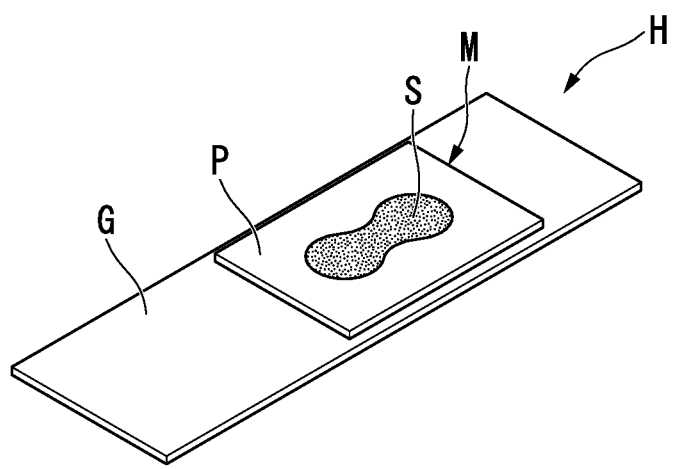
FIG. 2 is a perspective view of a thin section sample which is prepared by the automatic thin-cutting device according to the present invention.

FIG. 1 is a perspective view of an embedding block B which is transported by an automatic thin-cutting device 1. FIG. 2 is a perspective view of a thin section sample H which is prepared by the automatic thin-cutting device 1.

As shown in FIG. 1, the automatic thin-cutting device 1 (refer to FIG. 3) of the present embodiment is a device which thinly cuts the embedding block B, in which a biological sample S is embedded by Paraffin P serving as an embedding material, to a thickness of 3 μm to 5 μm, for example. Accordingly, it is possible to prepare a thin section M shown in FIG. 2 by the automatic thin-cutting device 1.

In addition, the automatic thin-cutting device 1 of the present embodiment not only can prepare the thin section M but also can automatically perform an operation of accommodating the thin section samples H in a basket after transferring the thin section M to a substrate such as a slide glass G and preparing the thin section samples H.

In addition, the embedding block B is a rectangular block in a plan view in which moisture in the formalin-fixed biological sample S is paraffin-substituted, and thereafter, the periphery is hardened in a block shape by the paraffin P. Accordingly, the biological sample S is embedded in the paraffin P. In addition, for example, the biological sample S may be a tissue such as an internal organ extracted from a human body, experimental animal, or the like, and is a tissue which is appropriately selected in a medical field, a pharmaceutical field, a food field, a biological field, or the like.

In addition, as shown in FIG. 1, the embedding block B is fixed to a cassette K.

The cassette K is formed in a box shape by a resin having chemical resistance or the like, and has a role as a fixing table which fixes the embedding block B. One side surface of the cassette K is an inclined surface K1 in which the surface faces downward. ID data (not shown), which includes a production number of the cassette K, a preparation date of the embedding block B, various data of the biological sample S, or the like, is recorded on the inclined surface K1. Accordingly, it is possible to manage quality of the embedding block B by reading the ID data.

Subsequently, each component of the automatic thin-cutting device 1 will be described.

In the present embodiment, first, components configuring the automatic thin-cutting device 1 are sequentially and simply described, and thereafter, the necessary components are described in detail.

Figure 3:
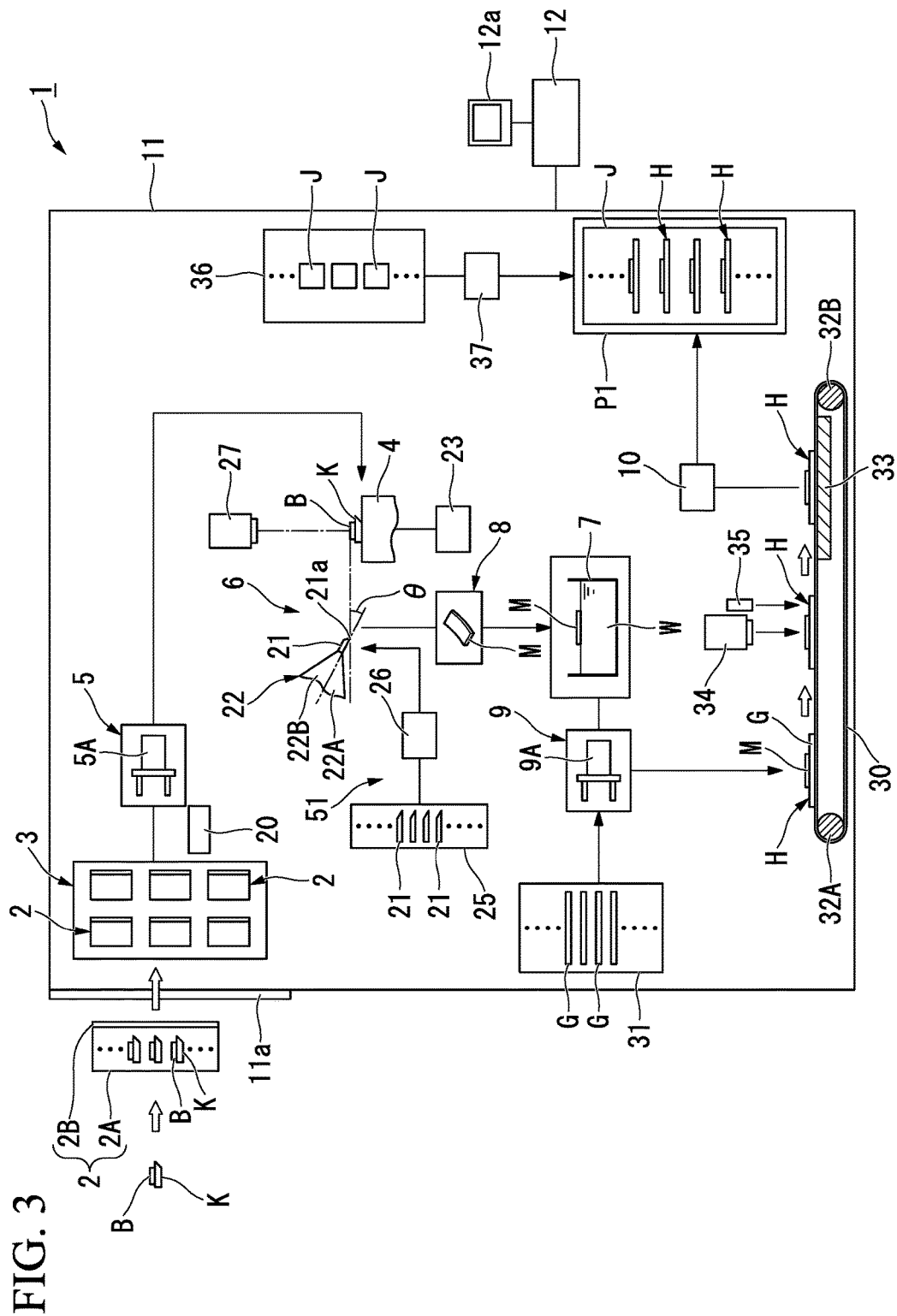
FIG. 3 is a schematic configuration view of the automatic thin-cutting device.

As shown in FIG. 3, the automatic thin-cutting device 1 mainly includes a plurality of magazines 2, a carousel 3, a block transport mechanism 5, a thin-cutting mechanism 6, a thin section transport mechanism 8, a slide glass handling mechanism 9, a slide glass accommodation mechanism 10, a device case 11 which accommodates the components in the inner portion of the device case, and a control portion 12 which totally controls the components. The plurality of embedding blocks B is accommodated in the plurality of magazines 2 so as to be inserted or removed. Each magazine 2 is individually detachably mounted on the carousel 3. The block transport mechanism 5 inserts or removes one embedding block B which is selected among the plurality of embedding blocks B accommodated in the magazine 2 mounted on the carousel 3, and places the embedding block B on a stage 4. The thin-cutting mechanism 6 cuts the embedding block B placed on the stage 4 to a predetermined thickness, and the cutting of thin section M is performed. The thin section transport mechanism 8 transports the thin section M cut by the thin-cutting mechanism 6 to the storage tank 7, and floats the thin section M on a liquid surface to spread the thin section M. The slide glass handling mechanism 9 scoops the spread thin section M from the liquid surface onto the slide glass G, and prepares the thin section sample H. The slide glass storage mechanism 10 accommodates the prepared thin section sample H in a basket J.

(Device Case)

The inner portion of the above-described device case 11 can be sealed, and for example, in the inner portion, an environmental condition such as humidity, temperature, or the like can be set to a desired condition. An access door 11a which is opened and closed by an operator is provided on the wall surface of the device case 11. The access door 11a is a door which is used when the magazine 2 is mounted or extracted. By opening the access door 11a, access to the carousel 3 on which the magazine 2 is mounted is possible.

(Magazine)

The magazine 2 is an accommodation case in which the entirety is formed in a vertically long rectangular parallelepiped shape. The magazine 2 can accommodate the plurality of embedding blocks B fixed to the cassettes K in a state where the embedding blocks B are arranged in a height direction. The magazine 2 mainly includes a box-shaped magazine main body 2A in which the front surface is open, and an opening and closing door 2B which is fixed to the magazine main body 2A.

When the opening and closing door 2B is closed, a portion of the plurality of embedding blocks B accommodated in the magazine main body 2A is covered, and thus, dropping of the embedding block B is prevented. Accordingly, the operator can carry the magazine 2 at ease without paying attention to dropping of the embedding block B.

(Carousel)

The magazine 2 configured as described above is detachably mounted on the carousel 3. In the illustrated example, six magazines 2 are simultaneously mounted on the carousel 3.

The carousel 3 is disposed at a position at which access is possible from the outside by opening an access door 11a of the device case 11. Accordingly, the magazine 2 can be mounted on the carousel 3 or removed from the carousel 3 manually by the operator.

In addition, the carousel 3 can rotate about a vertical axis. The carousel 3 moves the magazine 2 mounted by the rotation in a circumferential direction, and can set one selected magazine 2 to a block extraction position at which the magazine 2 faces the block transport mechanism 5. Moreover, the operation of the carousel 3 is controlled by the control portion 12.

(Reading Portion)

A reading portion 20 is disposed at a position adjacent to the carousel 3. The reading portion 20 reads ID data printed on the cassette K of each embedding block B which is accommodated in the magazine 2 positioned at the above-described block extraction position.

For example, the reading portion 20 and the magazine 2 positioned at the block extraction position move relative to each other in a vertical direction. According to this relative movement, the reading portion 20 can read the ID data printed on the cassette K of all embedding blocks B accommodated in the magazine 2. In addition, the reading portion 20 optically reads the ID data and outputs the read ID data to the control portion 12.

(Block Transport Mechanism)

The block transport mechanism 5 is a handling robot which includes a hand portion 5A capable of holding the cassette K which fixes the embedding block B. The block transport mechanism 5 is positioned at a position adjacent to the carousel 3. Based on an instruction from the control portion 12, the block transport mechanism 5 holds one embedding block B, which is accommodated in the magazine 2 positioned at the block extraction position among the magazines 2 mounted on the carousel 3, by the hand portion 5A, can insert and remove the held embedding block B from the magazine 2, or can place the embedding block on the stage 4.

(Stage)

In the stage 4, an actuator is incorporated into the inner portion of the stage 4, and the stage 4 is configured to appropriately move vertically based on an instruction from the control portion 12. Accordingly, it is possible to adjust the height of the embedding block B placed on the stage 4, and it is possible to thinly cut the embedding block B to a desired thickness (for example, 5 μm).

In addition, the stage 4 is a multi-axial stage in which rotation about the vertical axis and pivot about a horizontal axis (two axes) can be performed. Therefore, the stage 4 freely controls the posture of the embedding block B, and can set the orientation, the inclination, or the like of the embedding block B to a desired state.

(Thin-Cutting Mechanism)

The thin-cutting mechanism 6 includes a cutting blade 21 which is disposed in the vicinity of the stage 4, a holder 22 which holds the cutting blade 21 in an exchangeable manner, and a moving mechanism 23. The moving mechanism 23 moves the stage 4 with respect to the cutting blade 21, and thinly cuts the embedding block B with the cutting blade 21.

Figure 4:
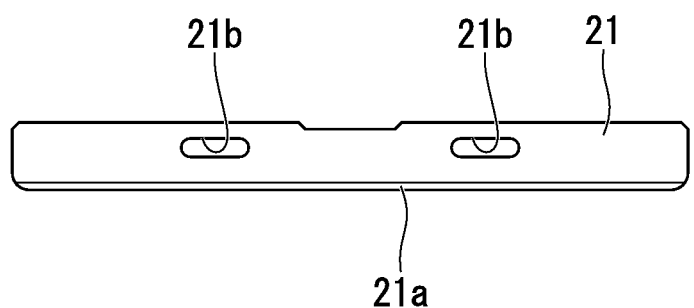
FIG. 4 is a plan view of a cutting blade.

FIG. 4 is a plan view of the cutting blade 21.

As shown in FIG. 4, the cutting blade 21 is formed of a long magnetic body in which one end side is a blade edge 21a. The cutting blade 21 is obliquely held (clamp-fixed) to the holder 22 with a predetermined rake angle θ1. In addition, in the cutting blade 21, two elliptical through-holes 21b are formed at intervals in the direction in which the blade edge 21a extends. In addition, in the illustrated example, the blade edge 21a is a single edge. However, the blade edge may be a double edge.

As shown in FIG. 3, the holder 22 mainly includes a placing plate 22A and a pressing plate 22B. The cutting blade 21 is placed on the placing plate 22A in a state where the blade edge 21a is exposed to the outside. The pressing plate 22B presses the placed cutting blade 21 to the placing plate 22A, and the cutting blade 21 is clamp-fixed.

The moving mechanism 23 includes a guide rail (not shown) and a driving portion (not shown) which reciprocates the stage 4 along the guide rail at a predetermined speed, thinly cuts the embedding block B with the cutting blade 21 clamp-fixed by the holder 22 by reciprocating the stage 4 based on an instruction from the control portion 12, and performs cutting of the thin section M.

In addition, the stage 4 raises the embedding block B by a predetermined amount according to the reciprocation by the moving mechanism 23. Accordingly, the embedding block B is cut to a predetermined thickness, and it is possible to prepare the thin section M.

In addition, in the present embodiment, the moving mechanism 23 is configured so that the stage 4 side moves with respect to the cutting blade 21. However, the moving mechanism 23 may be configured so that the cutting blade 21 side moves with respect to the stage 4, or may be configured so that the holder 22 side and the stage 4 side move together.

In either case, the moving mechanism 23 may be designed in any manner as long as the embedding block B and the cutting blade 21 move relative to each other and the thin-cutting can be performed by the cutting blade 21.

(Replacement Blade Cartridge and Cutting Blade Transport Mechanism)

The plurality of cutting blades 21 are stored in the replacement blade cartridge 25 in a state of overlapping in multiple stages. After the cutting blades 21 are extracted one by one as necessary by the cutting blade transport mechanism 26, a cutting blade 21 is transported to the holder 22 and clamp-fixed. That is, the cutting blade 21 can be replaced at a predetermined timing.

The above-described replacement blade cartridge 25 is detachably set to the cutting blade transport mechanism 26.

Based on an instruction from the control portion 12, the cutting blade transport mechanism 26 inserts a new cutting blade 21 extracted from the replacement blade cartridge 25 into a portion between the placing plate 22A and the pressing plate 22B in the holder 22, and extrudes and transports the used cutting blade 21 from the holder 22. Accordingly, the replacement of the cutting blade 21 is performed. The pressing plate 22B of the holder 22 receives the intention that a new cutting blade 21 is set, and is operated to perform the clamp-fixing of the new cutting blade 21 according to an instruction from the control portion 12.

In addition, the used cutting blade 21 extruded from the holder 22 is sent to a waste bottle (not shown) or the like via a waste chute (not shown) or the like.

(First Imaging Camera)

A first imaging camera 27 which images the embedding block B placed on the stage 4 is disposed above the stage 4. The first imaging camera 27 images the embedding block B which is illuminated by illumination light from a light source (not shown). In this case, the first imaging camera 27 can image the surface state or the internal state of the embedding block B according to the kind (for example, vertical illumination light or diffused illumination light) of the illumination light.

In addition, the captured image is sent to the control portion 12, is recorded, and for example, is displayed on a monitor 12a connected to the control portion 12.

(Thin Section Transport Mechanism)

Based on an instruction from the control portion 12, the thin section transport mechanism 8 is a mechanism which transports the thin section M cut by the thin-cutting mechanism 6 up to the storage tank 7 and floats the thin section M on the liquid surface. For example, the thin section transport mechanism 8 may use a transport belt, a transport tape, or the like.

(Storage Tank)

A liquid W such as water which is adjusted to have a predetermined temperature is stored in the storage tank 7. In the storage tank 7, the thin section M floated on the liquid surface is spread using surface tension. In addition, the stored liquid W is discharged from the storage tank 7 via a circulation pipeline (not shown) as necessary, and is supplied into the storage tank 7. Accordingly, a clear liquid W is stored in the storage tank 7 at all times.

(Slide Glass Handling Mechanism)

The slide glass handling mechanism 9 is a handling robot which includes the hand portion 9A capable of holding the slide glass G, and is disposed at a position adjacent to the storage tank 7. The slide glass handling mechanism 9 is operated based on an instruction from the control portion 12 and scoops the spread thin section M floated on the liquid on the slide glass G held by the hand portion 9A to transfer the thin section M, and thus, it is possible to prepare the thin section sample H.

After the slide glass handling mechanism 9 scoops the thin section M on the slide glass G and prepares the thin section sample H, the slide glass handling mechanism 9 delivers the thin section sample H onto a sample transport belt 30. Thereafter, the slide glass handling mechanism 9 holds a new slide glass G from the slide glasses G accommodated in a slide glass accommodation portion 31 and moves the new slide glass G to a standby state for scooping the next thin section M.

The slide glass accommodation portion 31 is disposed in the vicinity of the storage tank 7, and for example, several dozens to several hundreds of unused glass slides G are accommodated in the inner portion of the slide glass accommodation portion 31.

(Sample Transport Belt and Hot Plate)

For example, the above-described sample transport belt 30 is a transport belt which is wound between a driving pulley 32A and a driven pulley 32B which are driven based on an instruction from the control portion 12. The sample transport belt 30 can transport the thin section sample H to the downstream side by driving of the driving pulley 32A.

The hot plate 33 which is heated to a predetermined temperature is disposed at the downstream side in the transport direction of the sample transport belt 30. The hot plate 33 heats the thin section sample H placed on the sample transport belt 30 in a state where the thin section sample H is interposed between the hot plate 33 and the sample transport belt 30. Accordingly, superfluous liquid W remaining on the thin section sample H can be removed by vaporization, and it is possible to further spread the thin section M while preventing the existence of liquid W between the slide glass G and the thin section M.

(Second Imaging Camera and Recording Portion)

In the present embodiment, while the thin section sample H is transported to the downstream side at which the hot plate 33 is disposed by the sample transport belt 30, the imaging of the thin-cutting state in the thin section M using a second imaging camera 34 and the printing of individual data to the slide glass G using a recording portion 35 are performed.

The second imaging camera 34 is disposed above the sample transport belt 30, images the thin section M until the thin section sample M placed on the sample transport belt 30 is transported to the downstream side, and sends the captured image to the control portion 12. The captured image of the second imaging camera 34 sent to the control portion 12 is recorded in the control portion 12, and for example, is displayed on the monitor 12a.

For example, the recording portion 35 is a laser marker, and is disposed to be adjacent to the second imaging camera 34. Based on an instruction from the control portion 12, the recording portion 35 irradiates the slide glass G with laser light and performs printing of individual data. In this case, similar to the second imaging camera 34, the recording portion 35 performs printing until the thin section sample H is transported to the downstream side.

(Slide Glass Accommodation Mechanism)

The slide glass accommodation mechanism 10 is disposed above the sample transport belt 30, and is a mechanism which accommodates the thin section sample H on the sample transport belt 30 heated by the hot plate 33 in the basket J, based on an instruction from the control portion 12. For example, as this mechanism, the thin section sample H is extruded from the sample transport belt 30 using an extrusion rod driven by a cylinder or the like and may be accommodated in the basket J, or the thin section sample H may be accommodated in the basket J using a robotic hand or the like.

(Basket)

For example, the basket J is a dye basket, and can store several thin section samples H to several dozens of thin section samples H at once. A plurality of baskets J is accommodated in a basket accommodation portion 36 in advance. After the baskets J accommodated in the basket accommodation portion 36 are sequentially extracted by a basket supply mechanism 37 which is operated based on an instruction from the control portion 12, the baskets J are set at a sample accommodation position P1. At the sample accommodation position P1, the thin section samples H are accommodated in the basket J.

When the thin section samples H having the predetermined number of sheets are accommodated in the basket J, the basket J is sent into a storage cabinet (not shown) so as to be stored. In this case, warm wind adjusted to a predetermined temperature circulates through the storage cabinet, and thus, the thin section samples H are dried in an optimal state.

(Replacement Blade Supplying Mechanism)

Figure 5:
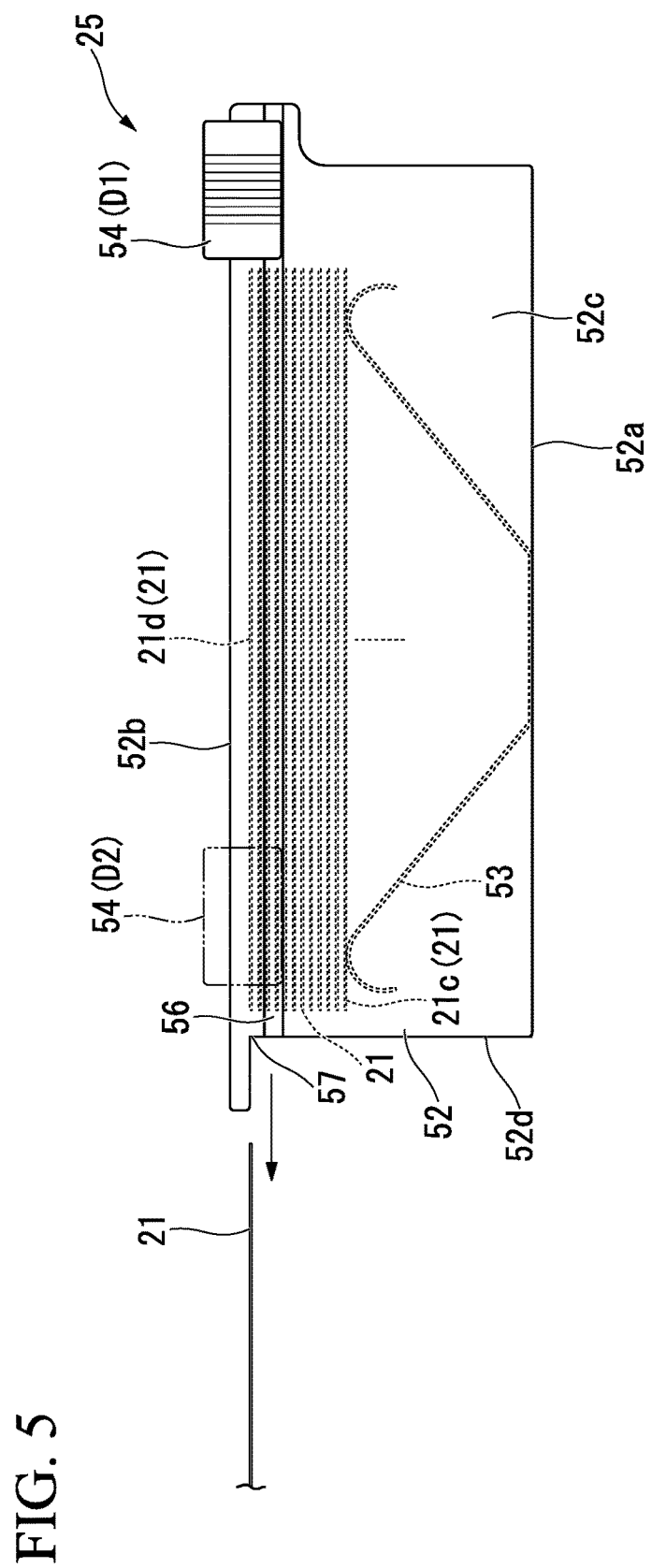
FIG. 5 is a side view of a replacement blade cartridge.
Figure 6:
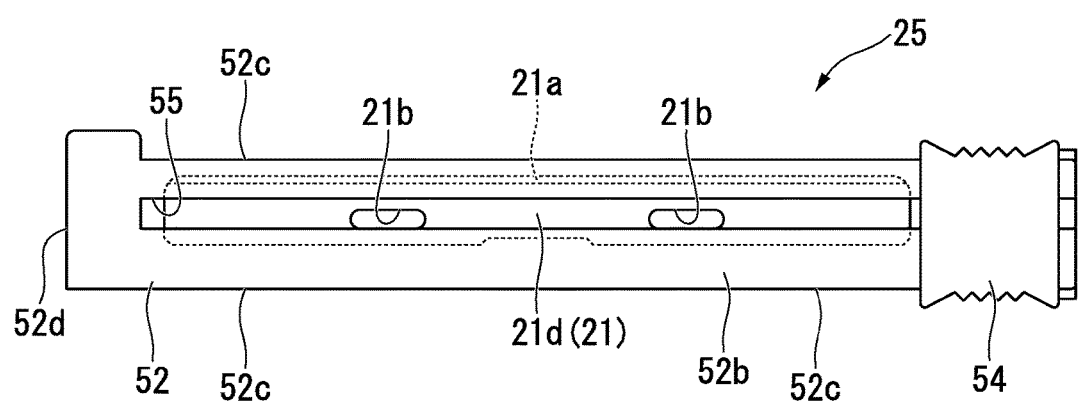
FIG. 6 is a plan view of the replacement blade cartridge.

Next, among the components, the configuration of the replacement blade supplying mechanism 51 including the cutting blade transport mechanism 26 will be described in detail. FIG. 5 is a side view of the replacement blade cartridge 25. FIG. 6 is a plan view of the replacement blade cartridge 25.

First, the replacement blade cartridge 25 set to the cutting blade transport mechanism 26 will be described.

As shown in FIGS. 5 and 6, the replacement blade cartridge 25 includes a case main body 52, a biasing portion 53, and a lever portion 54. A plurality of cutting blades 21 are accommodated in the case main body 52 in a state where the cutting blades 21 overlap with one another in the thickness direction. The biasing portion 53 is disposed between a bottom surface 52a of the case main body 52 and a lowermost cutting blade 21c which is positioned in the lowermost layer among the plurality of cutting blades 21, and biases the cutting blade 21 toward the upper layer. The lever portion 54 extracts only the uppermost cutting blade 21d positioned in the uppermost layer among the cutting blades 21 accommodated in the case main body 52.

The case main body 52 is formed in a rectangular parallelepiped shape. The longitudinal direction of the case main body 52 is the direction in which the blade edge 21a of the cutting blade 21 extends. A long groove 55 is formed on a top surface 52b of the case main body 52 along the longitudinal direction. Guide grooves 56 (refer to FIG. 5) which extend along the longitudinal direction are formed on a pair of side surfaces 52c opposing each other in the short-length direction among the side surfaces of the case main body 52.

Moreover, an opening portion 57 (refer to FIG. 5) through which the cutting blade 21 can pass is formed on a side surface 52d positioned on one side in the longitudinal direction among the side surfaces of the case main body 52. The uppermost cutting blade 21d among the cutting blades 21 accommodated in the case main body 52 is transported to the outside the opening portion 57.

For example, the biasing portion 53 is a V shaped plate spring, and the center portion in the direction in which the biasing portion 53 extends is fixed to the bottom surface 52a of the case main body 52. Both end portions of the biasing portion 53 abut both end portion of the lowermost cutting blade 21c in the direction in which the blade edge 21a extends, from below.

For example, the lever portion 54 is formed in a U shape in a cross-sectional view, and covers the case main body 52 from the top surface 52b side in a state where both end portions are fitted to the guide grooves 56 of the case main body 52. Moreover, in a state where the lever portion 54 is guided by the guide grooves 56, the lever portion 54 is slidable between an initial position D1 positioned at one side in the longitudinal direction of the case main body 52, and a slide position D2 positioned at the other side in the longitudinal direction.

In the lever portion 54, a protrusion 58 (FIGS. 8A and 8B) is formed on the end portion close to the slide position D2. The protrusion 58 is inserted into the long groove 55 formed on the top surface 52b of the case main body 52. The length of the protrusion 58 is adjusted so that the protrusion comes into contact with only the uppermost cutting blade 21d among the plurality of cutting blade 21 accommodated in the case main body 52. When the lever portion 54 slides from the initial position D1 to the slide position D2, the lever portion 54 abuts an end edge (hereinafter, referred to as a rear end edge) of the uppermost cutting blade 21d positioned at the rear side in the movement direction (transport direction) of the lever portion 54, and extrudes the uppermost cutting blade 21d toward the opening portion 57. Accordingly, the uppermost cutting blade 21d is transported from the opening portion 57 of the case main body 52.

Figure 7:
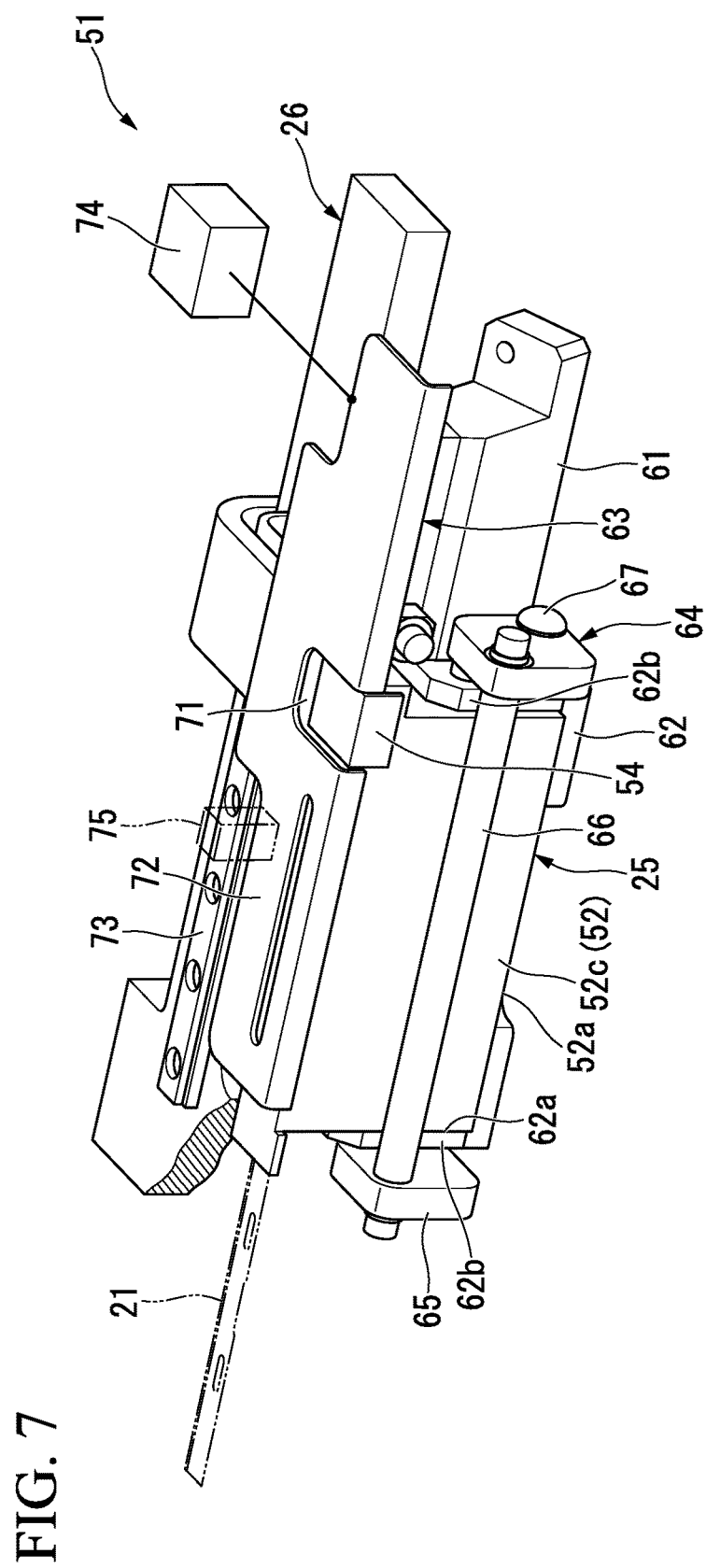
FIG. 7 is a perspective view of the replacement blade supplying mechanism.

FIG. 7 is a perspective view of the cutting blade transport mechanism 26. Moreover, in descriptions below, in the state where the replacement blade cartridge 25 is provided, the longitudinal direction of the replacement blade cartridge 25 is defined as the longitudinal direction of the device, the short-length direction of the replacement blade cartridge 25 is defined as the width direction of the device, and the overlapping direction of the cutting blades 21 is defined as the height direction of the device.

As shown in FIG. 7, the cutting blade transport mechanism 26 includes a frame member 61, a cartridge accommodation portion 62, and a lever guide 63. The cartridge accommodation portion 62 is fixed to the frame member 61, and the above-described replacement blade cartridge 25 is provided in the cartridge accommodation portion 62. The lever guide 63 accommodates the lever portion 54 of the replacement blade cartridge 25, and causes the lever portion 54 to slide in the longitudinal direction of the device.

The cartridge accommodation portion 62 is formed in a frame shape which holds the bottom surface 52a side of the case main body 52. The cartridge accommodation portion 62 formed in a frame shape includes a cartridge inlet 62a which is opened to the one side in the width direction of the device. In a state where the short-length direction of the replacement blade cartridge 25 is coincident with the width direction of the device, the replacement blade cartridge 25 is mounted into the cartridge accommodation portion 62 through the cartridge inlet 62a.

Moreover, the cartridge accommodation portion 62 is fixed to the frame member 61 with the above-described rake angle θ. Accordingly, in a state where the replacement blade cartridge 25 mounted into the cartridge accommodation portion 62 is inclined so that the angle between the top surface 52b of the case main body 52 and the horizontal surface parallel to the surface of the embedding block B is the rake angle θ, the replacement blade cartridge 25 is accommodated into the cartridge accommodation portion 62.

An opening and closing member 64, which can open and close the cartridge inlet 62a, is provided on the cartridge accommodation portion 62. The opening and closing member 64 includes a pair of rotation plates 65 and an opening and closing bar 66. The pair of rotation plates 65 is provided on side wall portions 62b which are positioned on both sides in the longitudinal direction of the device of the cartridge accommodation portion 62. The opening and closing bar 66 is connected to the rotation plates 65 and close and opens the cartridge inlet 62a.

Each rotation plate 65 is rotatably supported by the above-described side wall portion 62b via the rotating shaft 67 which extends in the longitudinal direction of the device.

The opening and closing bar 66 suspends the end portions positioned at one side in the width direction of the device in the rotation plates 65. The opening and closing member 64 is rotated between a closing position at which the opening and closing bar 66 overlaps with the cartridge accommodation portion 62 in the width direction of the device, and an opening position at which the opening and closing bar 66 does not overlap with (moves backward from) the cartridge accommodation portion 62 in the width direction of the device, by a driving portion (not shown).

The lever guide 63 is a plate shape member which is disposed on one side in the height direction of the device with respect to the cartridge accommodation portion 62. The lever guide 63 includes a lever accommodation portion 71 which accommodates the lever portion 54 of the replacement blade cartridge 25.

The lever accommodation portion 71 is opened toward one side in the width direction of the device, and surrounds the lever portion 54 from both sides in the length direction of the device and the other side in the width direction of the device. In addition, the lever accommodation portion 71 is positioned at the other side in the length direction of the device of the cartridge accommodation portion 62 when viewed from the height direction of the device in the initial position described below.

In addition, a regulation portion 72 which extends toward both sides in the length direction of the device with respect to the lever accommodation portion 71 is formed on the lever guide 63. The end portion of the one side in the width direction of the device in the regulation portion 72 is positioned at one side in the width direction of the device from the cartridge inlet 62a when viewed from the height direction of the device and is bent toward the other side in the height direction of the device. That is, when viewed in a plan in FIG. 7, the end portion of the one side in the width direction of the device in the regulation portion 72 is positioned outside the cartridge inlet 62a in the width direction of the device. In addition, as shown in FIG. 7, for example, the end portion of the one side in the width direction of the device in the regulation portion 72 is bent to the downward side in the height direction of the device. In addition, the portion positioned at the one side in the length direction of the device with respect to the lever accommodation portion 71 in the regulation portion 72 is positioned at the position at which the portion positioned at the one side overlaps with the cartridge accommodation portion 62 from the height direction of the device.

The lever guide 63 configured in this way is configured to be slidable on a linear guide 73 formed on the frame member 61 along the length direction of the device, by the operation of the driving portion 74. Moreover, the lever guide 63 slides in the state where the lever portion 54 accommodated in the lever accommodation portion 71, and the lever portion 54 moves between the above-described initial position D1 and the slide position D2 (refer to FIG. 5) and extrudes the uppermost cutting blade 21d from the case main body 52.

Figure 8A:
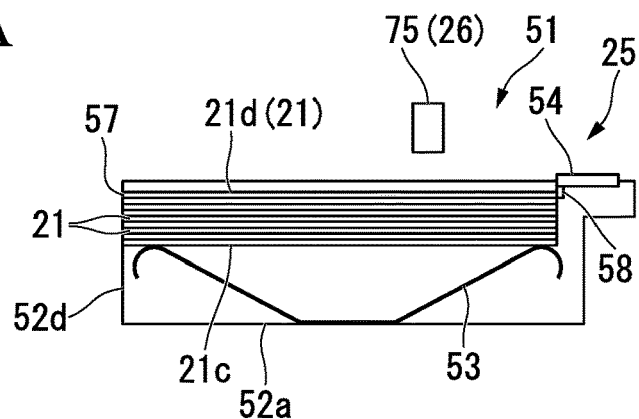
FIG. 8A is a schematic view showing a positional relationship between the replacement blade cartridge and a detection portion.
Figure 8B:
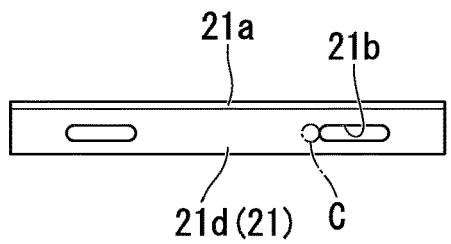
FIG. 8B is a schematic view showing a positional relationship between the cutting blade and the detection portion (detection position).

FIG. 8A is a schematic view showing the positional relationship between the replacement blade cartridge 25 and a detection portion 75, and FIG. 8B is a schematic view showing the positional relationship between the cutting blade 21 and the detection portion 75 (detection position C).

Moreover, as shown in FIGS. 7, 8A, and 8B, when the uppermost cutting blade 21d (refer to FIG. 5) is transported toward the opening portion 57 of the case main body 52, the cutting blade transport mechanism 26 of the present embodiment includes the detection portion 75 which detects whether or not there is a cutting blade 21 in the layer below the uppermost cutting blade 21d through the portion (the through hole 21b of the uppermost cutting blade 21d in the present embodiment) through which the uppermost cutting blade 21d passes.

In the state where the lever portion 54 is positioned at the initial position D1, the detection portion 75 has the front side of the through hole 21b (for example, the rear through hole 21b in the movement direction of the lever portion 54) of the cutting blade 21 in the movement direction of the lever portion 54, as the detection position C. Accordingly, when the lever portion 54 moves toward the slide position D2, the through-hole 21b of the uppermost cutting blade 21d passes through the detection position C. In addition, for example, the detection portion 75 is a light sensor which irradiates detection light toward the cutting blade 21 and receives reflected light. Moreover, when the through hole 21b of the uppermost cutting blade 21d passes through the detection position C, the control portion 12 determines whether or not there is a cutting blade 21 in the layer below the uppermost cutting blade 21d according to the existence or the absence of the reflected light by the detection portion 75.

<Operation of Automatic Thin-Cutting Device>

Next, the operation of the automatic thin-cutting device 1 configured as described above will be described with reference to FIG. 3. Moreover, in the present embodiment, first, the overall flow until the thin section sample H is prepared is simply described, and thereafter, the flow of the partial process will be described in detail.

First, as advance preparation, the operator accommodates cassettes K, to which embedding blocks B are fixed, in the plurality of magazines 2. Thereafter, the operator opens the access door 11a of the device case 11, and mounts the magazines 2 on the carousel 3. After each magazine 2 is mounted on the carousel 3, the access door 11a is closed. In addition, the operator confirms whether or not the cutting blades 21 are sufficiently accommodated in the replacement blade cartridge 25 set by the cutting blade transport mechanism 26, whether or not the slide glass G is appropriately set to the slide glass accommodation portion 31, whether or not the basket J is appropriately set to the basket accommodation portion 36, or the like, and thus, the advance preparation ends.

After the advance preparation ends, the operator starts the operation of each component in the device case 11 through the control portion 12.

As described above, when the operations of the components in the device case 11 start, the control portion 12 sequentially rotates the carousels 3 and reads the ID data by the reading portion 20, and thereafter, the embedding blocks B are held using the hand portions 5A by the block transport mechanism 5. Subsequently, after the held embedding block B is extracted from the magazine 2 by the block transport mechanism 5, the embedding block B is placed on the stage 4 via the cassette K.

When the setting operation of the embedding block B on the stage 4 ends, the control portion 12 starts the thin-cutting operation of the embedding block B.

First, the upper surface of the embedding block B is adjusted to a desired height position by adjusting the height of the stage 4. In addition, the moving mechanism 23 reciprocates the stage 4 in the thin-cutting mechanism 6, and thus, the embedding block B is thinly cut by the cutting blade 21 which is clamped-fixed by the holder 22. Accordingly, it is possible to perform rough-flattening of the embedding block B.

When the thin-cutting is performed, the first imaging camera 27 images the embedding block B. This captured image is recorded in the control portion 12 and is displayed on the monitor 12a. Accordingly, the operator can confirm the surface state or the internal state of the embedding block B by the captured image which is displayed on the monitor 12a. Moreover, with reference to the captured image, it is possible to incline or rotate an appropriate stage 4 during the thin-cutting. As a result, it is possible to expose an optimal surface to the surface by rough machining of the embedding block B.

In addition, when a flattening operation is performed by the above-described rough machining, the operation in which the thin section M is transported to the storage tank 7 by the thin section transport mechanism 8 is not performed. Accordingly, the thin section M generated in the case becomes cutting chips and is recovered to a recovery portion (not shown).

Subsequently, after the flattening of the embedding block B ends, the control portion 12 transfers the operation of the automatic thin-cutting device 1 from the rough machining operation to a main cutting operation. In this case, the control portion 12 operates the cutting blade transport mechanism 26, and replaces the cutting blade 21 used in the rough machining with a new cutting blade 21. Moreover, the replacement of the cutting blade 21 is not limited to this case, and may be appropriately performed if necessary.

When the operation is transferred to the main cutting operation, the control portion 12 prepares the thin section M by the thin-cutting mechanism 6, transports the prepared thin section M to the storage tank 7 by the thin section transport mechanism 8, and floats the thin section on the liquid surface. Accordingly, the thin section M is spread, and curling or the like generated during the thin-cutting is removed.

Subsequently, the control portion 12 operates the slide glass handling mechanism 9, scoops the thin section M floated on the liquid surface onto the slide glass G, and prepares the thin section sample H. The slide glass handling mechanism 9 places the prepared thin section sample H on the sample transport belt 30 and delivers the thin section sample H.

Moreover, the control portion 12 drives the driving pulley 32A, and transports the thin section sample H placed on the sample transport belt 30 toward the downstream side. Then, while the thin section sample H is transported to the hot plate 33, the second imaging camera 34 images the thin section M, and the captured image is sent to the control portion 12.

Based on the captured image received from the second imaging camera 34, the control portion 12 determines whether or not the thin section M subjected to the main cutting is appropriately cut thinly. Here, when the control portion 12 determines that the thin-cutting is good, the control portion 12 operates the recording portion 35, and the individual data associated with the ID data read from the cassette K is recorded in the slide glass G of the thin section sample H.

In addition, the thin section sample H in which the individual data is recorded is further transported to the downstream side of the sample transport belt 30, and is heated by the hot plate 33. Moreover, the control portion 12 operates the slide glass accommodation mechanism 10, and accommodates the heated thin section sample H in the basket J.

As the determination result with respect to the quality of thin-cutting, when the control portion 12 determines that the thin-cutting is not good, the control portion 12 does not operate the slide glass accommodation mechanism 10, and delivers the thin section sample H from the sample transport belt 30 to a defective product discharging chute (not shown). Accordingly, the thin section sample H which is the defective product is not accommodated in the basket J, and is recovered.

When the thin section samples H which are determined as good products are accommodated in the basket J by a predetermined number, the basket J is sent to the storage cabinet and is stored, the basket supply mechanism 37 extracts a new basket J from the basket accommodation portion 36 and sets the new basket J at the sample storage position P1, and all subsequent accommodation operations are prepared.

As described above, according to the automatic thin-cutting device 1 of the present embodiment, not only the thin section M is automatically prepared but also the thin section sample H is automatically prepared, and it is possible to accommodate the thin section samples H in the basket J by a predetermined number.

Accordingly, the operator extracts the appropriate basket J from the storage cabinet, can transfer the basket J to the dyeing process of the biological sample S as it is, and the basket J is remarkably easily used. Particularly, since it is possible to collect the thin section samples H, in which the same dyeing operation is performed, in the same basket J, high convenience is obtained.

Next, an operation (replacement blade supply method) of the above-described replacement blade supplying mechanism 51 will be described in detail.

For example, when the cutting blade 21 is replaced during the transfer from the rough machining to the main cutting operation, first, the clamping fixation of the cutting blade 21 by the pressing plate 22B of the holder 22 is released. Accordingly, the cutting blade 21 is placed on the placing plate 22A. In this state, the lever guide 63 of the cutting blade transport mechanism 26 slides toward the one side in the length direction of the device. Then, according to the sliding of the lever guide 63, the lever portion 54 accommodated in the lever guide 63 moves from the initial position D1 toward the slide position D2. In this case, the uppermost cutting blade 21*d* among the cutting blades 21 accommodated in the case main body 52 is pushed toward the front side in the movement direction of the lever portion 54 by the protrusion 58 of the lever portion 54. As a result, the uppermost cutting blade 21*d* is extruded outside the case main body 52 through the opening portion 57 of the case main body 52.

As described above, the cutting blade 21 (the uppermost cutting blade 21*d*) extruded outside the case main body 52 is guided to the placing plate 22A of the holder 22. In this case, the replacement blade cartridge 25 is accommodated in the cartridge accommodation portion 62 with the rake angle θ in advance. Accordingly, the uppermost cutting blade 21*d* extruded from the opening portion 57 is guided to the placing plate 22A with the rake angle θ. Accordingly, the cutting blade 21 is guided to the placing plate 22A while extruding the cutting blade 21 (used cutting blade 21) placed on the placing plate 22A in advance in the direction in which the blade edge 21*a* extends. Accordingly, it is possible to simultaneously perform the disposal of the used cutting blade 21 and the supply of the unused cutting blade 21 (uppermost cutting blade 21*d*). Thereafter, the cutting blade 21 (uppermost cutting blade 21*d*) placed on the placing plate 22A is clamp-fixed by the pressing plate 22B of the holder 22. Accordingly, it is possible to replace the cutting blade 21.

Moreover, after the used cutting blade 21 is extruded from the holder 22 by the unused cutting blade 21, the used cutting blade 21 is sent to a bottle for disposal (not shown).

Figure 9A:
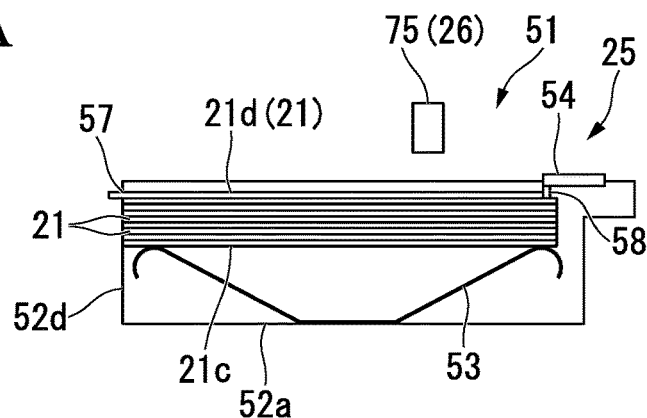
FIG. 9A is an explanatory view for explaining a determination method of replacement time of the replacement blade cartridge, and is a schematic view showing a positional relationship between the replacement blade cartridge and the detection portion.
Figure 9B:
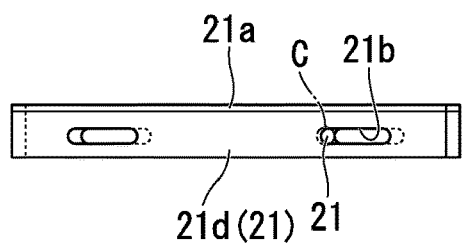
FIG. 9B is an explanatory view for explaining the determination method of the replacement time of the replacement blade cartridge, and is a schematic view showing the positional relationship (detection position) between the cutting blade and the detection portion.
Figure 10A:
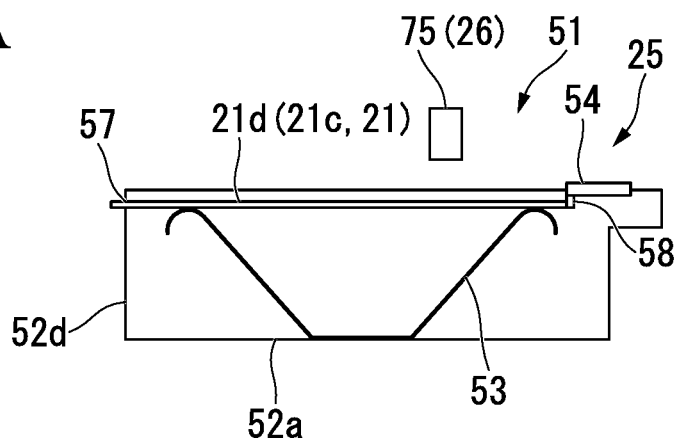
FIG. 10A is an explanatory view for explaining the determination method of the replacement time of the replacement blade cartridge, and is a schematic view showing the positional relationship between the replacement blade cartridge and the detection portion (detection position).
Figure 10B:
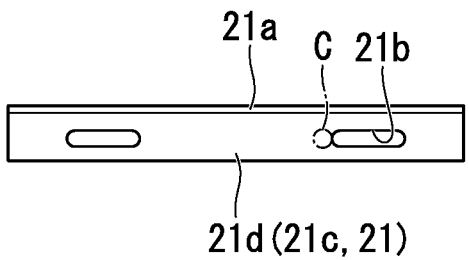
FIG. 10B is an explanatory view for explaining the determination method of the replacement time of the replacement blade cartridge, and is a schematic view showing the positional relationship between the cutting blade and the detection portion.

FIGS. 9A, 9B, 10A, and 10B are explanatory views for explaining a determination method of replacement time of the replacement blade cartridge 25. FIGS. 9A and 10A are schematic views showing the positional relationship between the replacement blade cartridge 25 and the detection portion 75 (detection position C). FIGS. 9B and 10B are schematic views showing the positional relationship between the cutting blade 21 and the detection portion 75.

When the cutting blade 21 is replaced, the control portion 12 determines whether or not the replacement blade cartridge 25 needs to be replaced, based on the detection result of the detection portion 75. In the present embodiment, when only one of the cutting blades 21 accommodated in the case main body 52 after the replacement remains, the control portion 12 determines that the replacement blade cartridge 25 needs to be replaced.

First, a case where two or more of the cutting blades 21 remain in the case main body 52 will be described.

When the uppermost cutting blade 21d is transported, if the lever portion 54 moves from the initial position D1 to the slide position D2, the through hole 21b of the uppermost cutting blade 21d passes through the detection position C. Then, as shown in FIGS. 9A and 9B, the cutting blade 21 positioned in the layer below the uppermost cutting blade 21 is exposed through the through hole 21b at the detection position C. Accordingly, the detection portion 75 detects that there is the cutting blade 21 in a layer below the uppermost cutting blade 21d through the through hole 21b of the uppermost cutting blade 21d. In addition, based on the detection result of the detection portion 75, the control portion 12 determines that the cutting blades 21 sufficiently (two or more) remains still in the case main body 52, and the replacement operation of the above-described cutting blade 21 is continued.

Next, a case where only one cutting blade 21 remains in the case main body 52 will be described.

Meanwhile, similar to the above-described case, as shown in FIGS. 10A and 10B, the detection portion 75 determines whether or not there is the cutting blade 21 in the layer below the uppermost cutting blade 21d through the through hole 21b of the uppermost cutting blade 21d. When only one cutting blade 21 remains (that is, when only one lowermost cutting blade 21c remains) in the case main body 52, since the cutting blade 21 does not exist in a layer below the uppermost cutting blade 21d, the detection portion 75 does not detect the cutting blade 21 through the through hole 21b of the uppermost cutting blade 21d. In this case, based on the detection result of the detection portion 75, the control portion 12 determines that only one cutting blade 21 remains, stops the replacement operation of the cutting blade 21, and prompts a warning toward the operator. Accordingly, the operator can determine the replacement time of the replacement blade cartridge 25.

Figure 11:
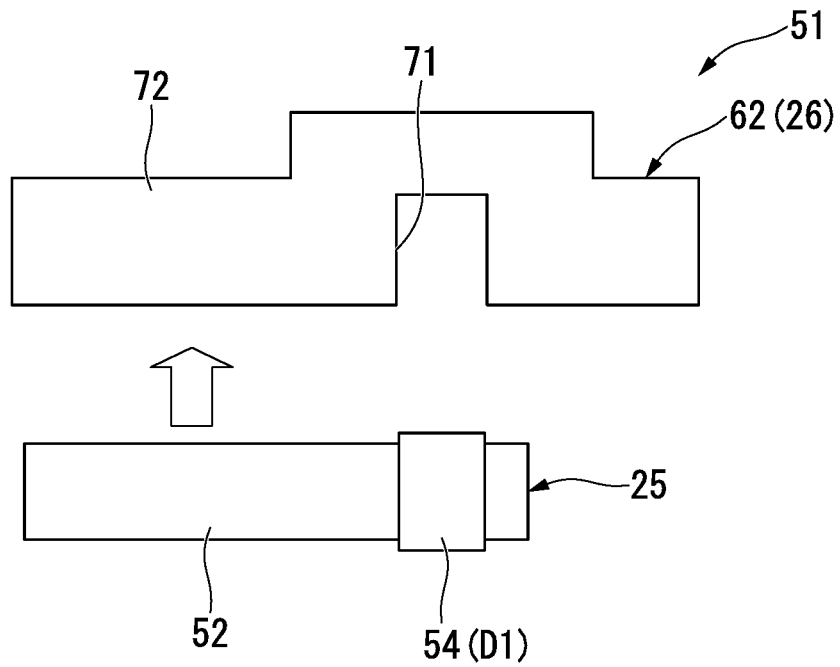
FIG. 11 is an explanatory view for explaining a replacement method of the replacement blade cartridge, and a schematic plan view of the replacement blade cartridge and a lever guide.
Figure 12:
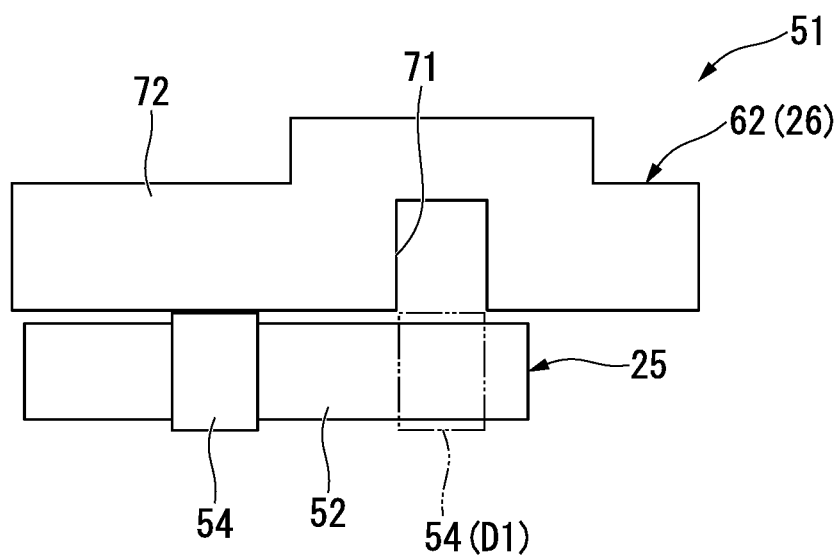
FIG. 12 is an explanatory view for explaining the replacement method of the replacement blade cartridge, and a schematic plan view of the replacement blade cartridge and the lever guide.

FIGS. 11 and 12 are explanatory views for explaining the replacement method of the replacement blade cartridge 25, and are schematic plan views of the replacement blade cartridge 25 and the lever guide 63.

As shown in FIG. 7, when the replacement blade cartridge 25 is replaced, first, the opening and closing member 64 of the cutting blade transport mechanism 26 is set to the opening position, and the used replacement blade cartridge 25 is extracted from the cartridge accommodation portion 62.

Thereafter, as shown in FIG. 11, the replacement blade cartridge 25 in which the cutting blades 21 are sufficiently accommodated is prepared, and thus, the prepared replacement blade cartridge 25 is set into the cartridge accommodation portion 62 through the cartridge inlet 62a. Specifically, in the state where the lever portion 54 is positioned at the initial position D1 and the short-length direction of the replacement blade cartridge 25 is coincident with the width direction of the device, the case main body 52 is inserted into the cartridge accommodation portion 62 and the lever portion 54 is inserted into the lever accommodation portion 71. Finally, the opening and closing member 64 is returned to the closing position, and the replacement operation of the replacement blade cartridge 25 is completed.

Then, in the present embodiment, as shown in FIG. 12, in a state where the lever portion 54 is positioned at locations other than the initial position D1, when the replacement blade cartridge 25 is set into the cartridge accommodation portion 62, the lever portion 54 comes into contact with the regulation portion 72 of the lever guide 63, and thus, the lever portion 54 is not accommodated into the cartridge accommodation portion 62.

In this way, in the present embodiment, the detection portion 75 is provided, which detects whether or not there is the cutting blade 21 in the layer below the uppermost cutting blade 21d through the through hole 21b of the uppermost cutting blade 21d when the uppermost cutting blade 21d is transported.

According to this configuration, when detection portion 75 detects that there is no cutting blade 21 in a layer below the uppermost cutting blade 21d, the transport of the cutting blade 21 by the lever guide 63 is stopped, and when the final one of the cutting blades 21 accommodated in the replacement blade cartridge 25 remains, it is possible to prompt the operator to replace the replacement blade cartridge 25. In this case, it is possible to stop the transport of the cutting blade 21 before the biasing of the cutting blade 21 by the biasing portion 53 is released. Therefore, it is prevent the cutting blade 21 from being not transported or from being transported in a direction different from a desired transport direction.

Accordingly, it is possible to prevent failure in supply of the cutting blade 21 in advance, and even when only one of the cutting blades 21 remains and the transport is stopped, since it is possible to easily determine the abnormal location or the cause of abnormality in the device, it is possible to smoothly perform the replacement operation of the replacement blade cartridge 25. Moreover, without stopping the driving of the entire automatic thin-cutting device 1, for example, it is possible to perform the replacement operation of the replacement blade cartridge 25 by only stopping the driving of the replacement blade supplying mechanism 51.

Moreover, in order to prevent failure of supply of the cutting blade 21, unlike the related art, since it is not necessary to dispose a plate which is a dummy between the biasing portion 105 and the lowermost cutting blade 101b, it is possible to improve a degree of freedom with respect to selection of the cutting blade 21.

Moreover, the regulation portion 72 which extends in the length direction of the device from the lever accommodation portion 71 is formed on the lever guide 63 of the present embodiment. Accordingly, it is possible to prevent the replacement blade cartridge 25 from being set in the state where the lever portion 54 is set at locations other than the lever accommodation portion 71. In addition, the operator can easily determine the set location of the lever portion 54. Accordingly, it is possible to prevent the replacement blade cartridge 25 from being erroneously set, and it is possible to more smoothly perform the replacement operation of the replacement blade cartridge 25.

In addition, the technical scope of the present invention is limited to the above-described embodiment, and includes various modifications which are applied to the above-described embodiment within a scope which does not depart from the gist of the present invention. That is, the configurations in the above-described embodiment are only examples, and may be appropriately modified.

For example, in the above-described embodiment, the configuration in which the detection portion 75 is provided on the frame member 61 side is described. However, the present invention is not limited to this. A configuration may be adopted in which the detection portion 75 is provided on the lever guide 63 and the detection portion 75 moves along with the movement of the lever guide 63. In this case, preferably, in the uppermost cutting blade 21d, the upper portion of the through hole 21b in the movement direction of the lever portion 54 is set to the detection position C, and when the uppermost cutting blade 21d smoothly slides, whether or not there is the cutting blade 21 in the portion through which the uppermost cutting blade 21d passes is detected through the through hole 21b of the uppermost cutting blade 21d.

Moreover, in the above-described embodiment, the configuration is described in which whether or not there is the cutting blade 21 in the layer below the uppermost cutting blade 21d is detected using the through hole 21b of the uppermost cutting blade 21d. However, the present invention is not limited to this. That is, the present invention may be also applied to the cutting blade 21 which does not include the through hole 21b.

Figure 13A:
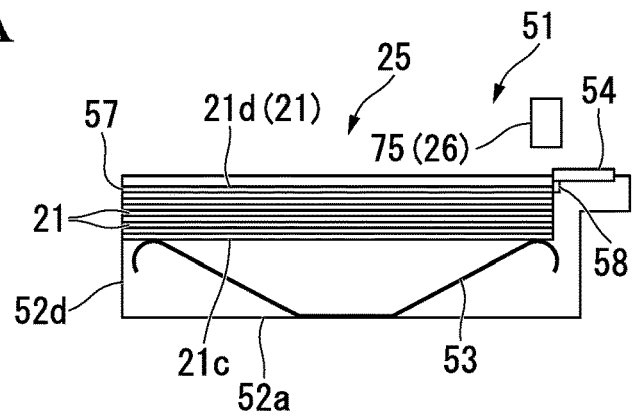
FIG. 13A is a schematic view showing the positional relationship between the replacement blade cartridge and the detection portion in another embodiment of the present invention.
Figure 13B:
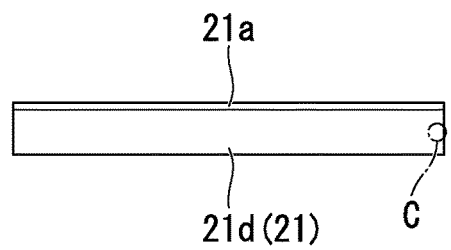
FIG. 13B is a schematic view showing the positional relationship between the cutting blade and the detection portion (detection position) in another embodiment of the present invention.

Specifically, as shown in FIGS. 13A and 13B, the rear end portion of the cutting blade 21 in the movement direction of the lever portion 54 is set to the detection position C. In this case, during the transport of the uppermost cutting blade 21d, when the lever portion 54 moves from the initial position D1 to the slide position D2, the rear end portion of the uppermost cutting blade 21d passes through the detection position C. At this time, only the lever portion 54 is temporarily moved backward from the detection position C by moving the lever portion 54 toward the initial position D1.

Figure 14A:
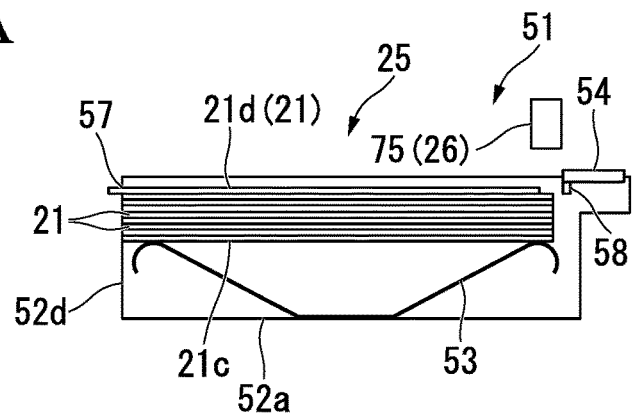
FIG. 14A is a schematic view showing the positional relationship between the replacement blade cartridge and the detection portion in still another embodiment of the present invention.
Figure 14B:
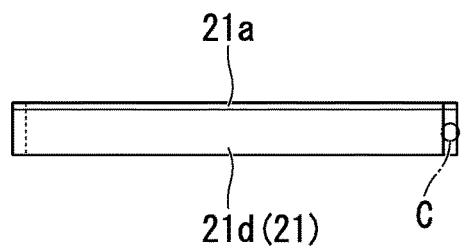
FIG. 14B is a schematic view showing the positional relationship between the cutting blade and the detection portion (detection position) in still another embodiment of the present invention.

When the cutting blades 21 sufficiently remain in the case main body 52, as shown in FIGS. 14A and 14B, the cutting blade 21 positioned in the layer below the uppermost cutting blade 21d is exposed to the portion (detection position C) through which the uppermost cutting blade 21d passes. Accordingly, the detection portion 75 can detect that there is the cutting blade 21 in the layer below the uppermost cutting blade 21d. In this case, the lever portion 54 is moved toward the slide position D2 again, and the transport of the uppermost cutting blade 21d is continued.

Figure 15A:
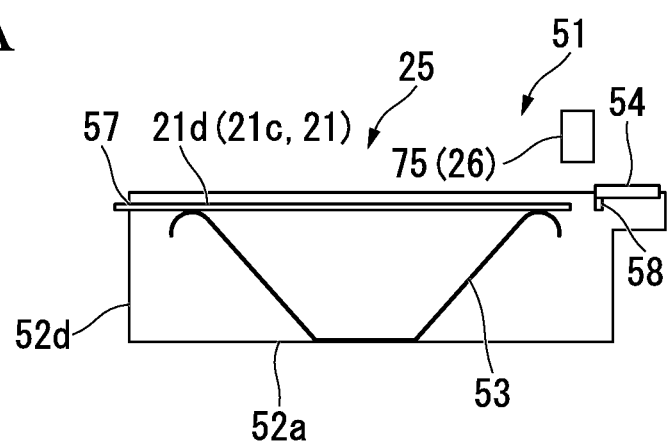
FIG. 15A is a schematic view showing the positional relationship between the replacement blade cartridge and the detection portion in still another embodiment of the present invention.
Figure 15B:
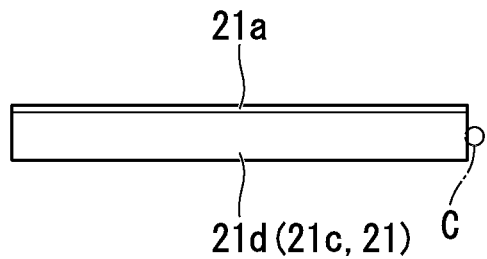
FIG. 15B is a schematic view showing the positional relationship between the cutting blade and the detection portion (detection position) in still another embodiment of the present invention.
Figure 16:
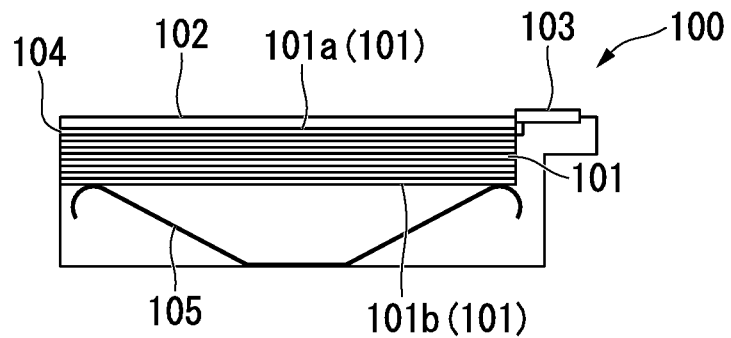
FIG. 16 is a schematic view for explaining a replacement blade cartridge in the related art.
Figure 17:
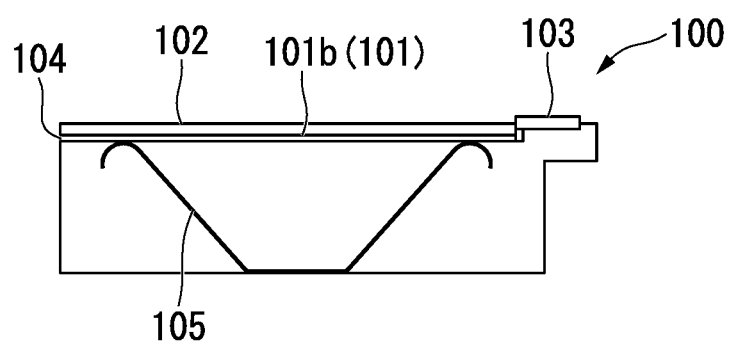
FIG. 17 is a schematic view for explaining the replacement blade cartridge in the related art.
Figure 18:
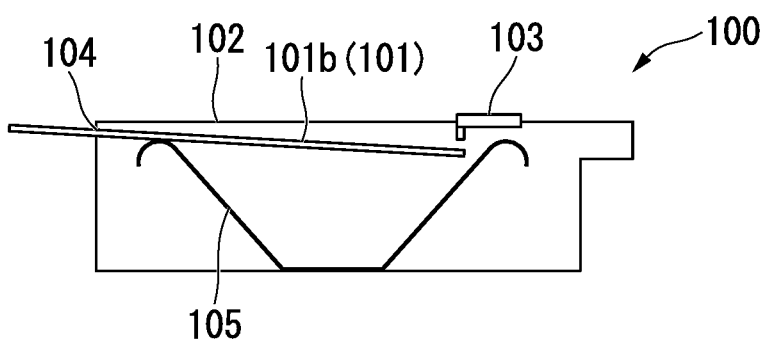
FIG. 18 is a schematic view for explaining the replacement blade cartridge in the related art.

Meanwhile, as shown in FIGS. 15A and 15B, when only one cutting blade 21 remains in the case main body 52, since there is no cutting blade 21 in a layer below the uppermost cutting blade 21d, even when the lever portion 54 moves backward from the detection position C, the cutting blade 21 cannot be detected in the detection position C. In this case, based on the detection result of the detection portion 75, the control portion 12 determines that only one cutting blade 21 remains, the control portion stops the replacement operation of the cutting blade 21 and prompts a warring toward the operator. Accordingly, the operator can determine that the replacement time of the replacement blade cartridge 25.

Moreover, in the above-described embodiment, the configuration is described in which the regulation portion 72 extends in both sides in the length direction of the device with respect to the lever accommodation portion 71. However, the present invention is not limited to this. For example, the regulation portion 72 may extend so that the regulation portion 72 at least overlaps with the cartridge accommodation portion 62 when viewed from the height direction of the device.

Moreover, in the above-described embodiment, the case where a light sensor is adopted as the detection portion 75 is described. However, the present invention is not limited to this. For example, as the detection method of the detection portion 75, the detection may be performed by image identification, electricity, magnetism, or the detection may be dynamically performed. In either case, any one may be adopted as long as whether or not there is the cutting blade 21 in the layer below the uppermost cutting blade 21d is detected through the portion (through hole 21b or the like) through which the uppermost cutting blade 21d passes.

In addition, in the above-described embodiment, the configuration in which the lever guide 63 slides with respect to the cartridge accommodation portion 62 (case main body 52) is described. However, the present invention is not limited to this. For example, a configuration in which the cartridge accommodation portion 62 slides with respect to the lever guide 63 may be adopted.

In addition, in the above-described embodiment, the case in which the replacement blade supplying mechanism 51 of the present invention is incorporated into the automatic thin-cutting device 1 is described. However, the present invention is not limited to this. For example, only the replacement blade supplying mechanism 51 may be singly used.

Moreover, in the above-described embodiment, the state where six magazines 2 are simultaneously mounted on the carousel 3 is described. However, the number of the magazines 2 is not limited to the case. For example, the number of the magazines 2 which are simultaneously mounted on the carousel 3 may be set to an arbitrary number such as one, two, three, four, five, or seven or more.

REFERENCE SIGNS LIST

21 . . . cutting blade, 21b . . . through hole, 21c . . . lowermost cutting blade, 21d . . . uppermost cutting blade, 25 . . . replacement blade cartridge, 26 . . . cutting blade transport mechanism (transport mechanism), 51 . . . replacement blade supplying mechanism, 54 . . . lever portion, 63 . . . lever guide

What is claimed is:
1. A replacement blade supply mechanism comprising:
   a transport mechanism comprising:
      a frame member;
      a cartridge accommodation portion fixed to the frame member, cartridge accommodation portion defining a cartridge inlet configured to detachably accommodate a replacement blade cartridge in which a plurality of cutting blades having a blade edge on one end are accommodated in a thickness direction thereof, and configured to individually transport an uppermost cutting blade positioned in an uppermost layer among the cutting blades accommodated in the replacement blade cartridge in a direction in which the blade edge extends;
      a lever guide including a lever accommodation portion configured to accommodate a lever portion of the replacement blade cartridge; and
      a detection portion comprising a sensor, said sensor configured to detect whether or not there is a cutting blade in a layer below an uppermost cutting blade through a through hole of the uppermost cutting blade when the uppermost cutting blade is transported, and
   wherein the detection portion is configured to stop the transport of a last remaining uppermost cutting blade when the detection portion has detected that there is no cutting blade in a layer below the uppermost cutting blade.

2. A replacement blade supply mechanism according to claim 1,
   wherein the cartridge accommodation portion accommodates a case main body in which the cutting blades are accommodated, in the replacement blade cartridge; and the lever guide which accommodates the lever portion which extrudes the uppermost cutting blade in the direction in which the blade edge extends, and relatively moves the lever portion in the direction, in which the blade edge of the cutting blade extends, with respect to the case main body, in the replacement blade cartridge, and wherein a regulation portion which extends along a movement direction of the lever guide is formed on an opening edge of the lever guide.

3. A replacement blade supply mechanism comprising:

a transport mechanism comprising:

a frame member;

a cartridge accommodation portion fixed to the frame member, cartridge accommodation portion defining a cartridge inlet configured to detachably accommodate a replacement blade cartridge in which a plurality of cutting blades having a blade edge on one end are accommodated in a thickness direction thereof, and configured to individually transport an uppermost cutting blade positioned in an uppermost layer among the cutting blades accommodated in the replacement blade cartridge in a first direction in which the blade edge extends;

a lever guide including a lever accommodation portion configured to accommodate a lever portion of the replacement blade cartridge; and a detection portion comprising a sensor, said sensor configured to detect whether or not there is a cutting blade in a layer below an uppermost cutting blade by setting a detection position in front of the lever portion in the first direction and above a rear end portion of an upper surface of the uppermost cutting blade and detecting a presence of the cutting blade in the layer below the uppermost cutting blade through a space that is generated above the layer below the uppermost cutting blade by the transportation of the uppermost cutting blade and that is included in the detection position, and wherein the lever portion is configured to press the uppermost cutting blade to generate the space by moving to the detection position and to move backward from the detection position toward an initial position of the lever portion so that the layer below the uppermost cutting blade can be detected by the sensor through the space, and wherein the detection portion is configured to stop the transport of a last remaining uppermost cutting blade when the detection portion has detected that there is no cutting blade in a layer below the uppermost cutting blade.

* * * * *